United States Patent [19]

Auld et al.

[11] 4,286,216

[45] Aug. 25, 1981

[54] FERROMAGNETIC RESONANCE PROBE AND METHOD FOR FLAW TESTING IN METALS

[75] Inventors: Bertram A. Auld, Menlo Park; Gary W. Elston, Santa Clara, both of Calif.

[73] Assignee: Board of Trustees of the Leland Stanford Junior University, Stanford, Calif.

[21] Appl. No.: 961,046

[22] Filed: Nov. 15, 1978

[51] Int. Cl.³ .......................................... G01R 33/12
[52] U.S. Cl. .................................... 324/237; 324/235; 324/300
[58] Field of Search ............... 324/228, 229, 236–240, 324/235, 300, 301, 306, 318, 319, 58 R, 58 B, 58.5 R, 58.5 B; 331/96, 107 G, 107 DP

[56] References Cited

U.S. PATENT DOCUMENTS

| | | | |
|---|---|---|---|
| Re. 26,286 | 10/1967 | Harmon | 324/237 |
| 2,799,823 | 7/1957 | Shaw et al. | 324/307 |
| 2,832,040 | 4/1958 | Harmon | 324/237 |
| 2,948,845 | 8/1960 | Handel | 324/319 |
| 3,085,196 | 4/1963 | Martin | 324/301 |
| 3,374,436 | 3/1968 | Thiess | 324/304 X |
| 3,529,234 | 9/1970 | Keen | 324/300 |
| 3,548,298 | 12/1970 | Adler | 324/301 |
| 3,576,503 | 4/1971 | Hanson | 331/96 |
| 3,828,243 | 8/1974 | Ward | 324/301 |
| 3,909,746 | 9/1975 | Abraham et al. | 331/107 DP X |
| 3,931,571 | 1/1976 | Hocking et al. | 324/236 |
| 4,048,588 | 9/1977 | Zublin et al. | 331/96 |

OTHER PUBLICATIONS

Auld, B. A., Theory of Ferromagnetic Resonance Probes for Surface Cracks in Metals, G.L. Report No. 2839, Jul. 1978, pp. 1–51, contract (CMR) NSF DMR 76-00726.

*Primary Examiner*—Gerard R. Strecker
*Attorney, Agent, or Firm*—Flehr, Hohbach, Test

[57] ABSTRACT

A probe and method for detecting surface flaws in metals. The probe operates at microwave frequencies and uses a ferromagnetic resonator. The resonator experiences a frequency shift when brought into proximity with a metal because of the perturbations of the demagnetizing fields at the boundaries of the resonator. A crack in the metal additionally disturbs the field and causes additional perturbations of the frequency. The perturbations in frequency are detected to provide an indication of flaws in the surface of the metal.

9 Claims, 4 Drawing Figures

FERROMAGNETIC RESONANCE PROBE AND METHOD FOR FLAW TESTING IN METALS

BACKGROUND OF THE INVENTION

This invention relates generally to a ferromagnetic resonance probe and method for testing for surface flaws in metals.

The traditional approach to eddy current testing for flaws in metals uses a small search coil to induce eddy currents in the metal surface being examined. Flaws are detected by observing changes in the input impedance of the search coil or by observing the frequency shift of a resonant circuit including the coil.

A microwave variant of the resonant circuit approach is to induce eddy currents in the test sample by fields fringing through a small aperture in the wall of a microwave cavity. The presence of flaws perturbs the resonant frequency of the cavity through interaction with the fringing fields. Spatial resolution is determined by the size of the aperture.

OBJECTS AND SUMMARY OF THE INVENTION

It is a general object of the present invention to provide a flaw testing probe and method having high resolution and sensitivity.

It is another object of the present invention to provide an improved microwave eddy current probe and method.

It is a further object of the present invention to provide a microwave probe employing a ferromagnetic resonator.

The foregoing and other objects of the invention are achieved by a probe including a ferromagnetic resonator, means for simultaneously applying a d.c. bias magnetic field and an rf field to said resonator to cause it to resonate at a predetermined frequency and means for indicating frequency changes in the resonating frequency or impedance of said resonator as the probe is scanned over a metallic surface under test.

DESCRIPTION OF PREFERRED EMBODIMENT(S)

In accordance with our invention, a ferromagnetic resonator is employed in a microwave flaw testing probe. Such a resonator may take the form of an yttrium iron garnet (YIG) sphere with a volume of less than $10^{-4}$ in.$^3$ and a resonance Q in the order of 1000. Such a resonator does not require an enclosing wall as do the prior art resonators. The resonator is easy to move over the surface of the metal under test. The d.c. magnetic field bias field, $H_{DC}$, required for ferromagnetic resonances can be supplied by small permanent magnets which can be part of a probe. Microwave excitation of the resonator can be provided by a small coupling loop placed near the resonator and electromagnetically coupled thereto.

Figure 1:
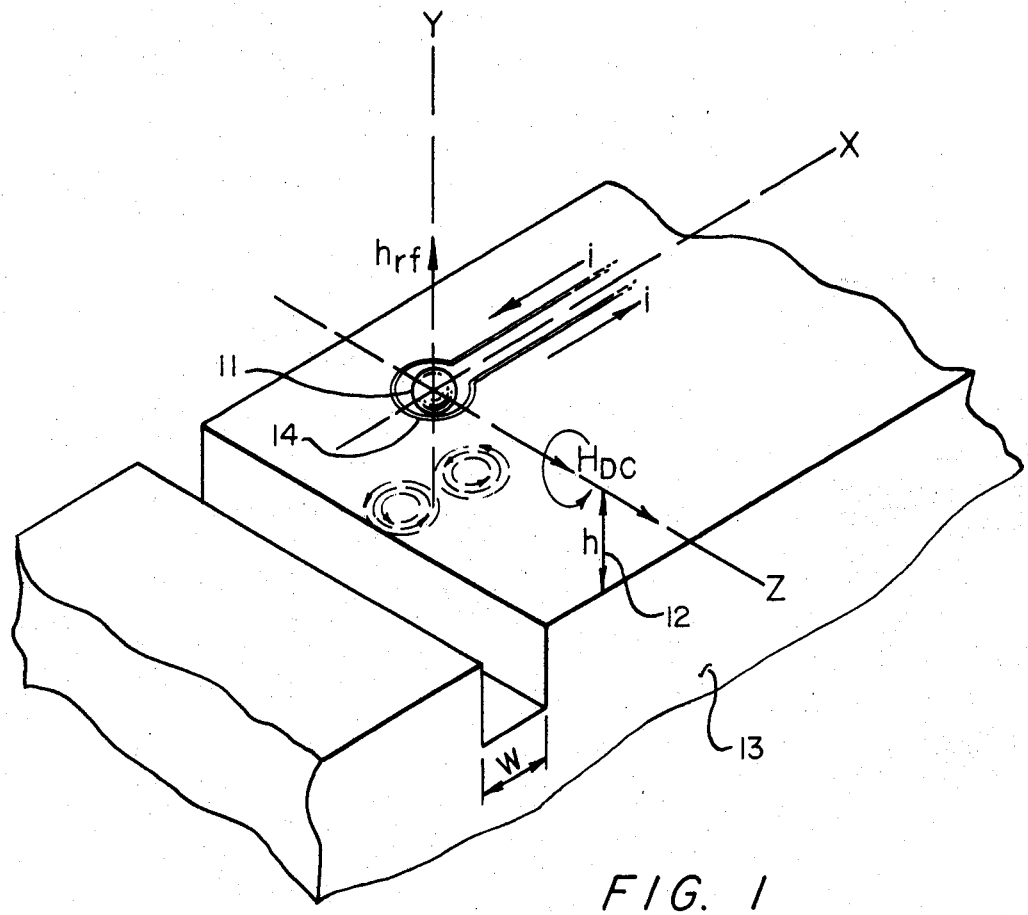
FIG. 1 schematically illustrates a probe in accordance with the present invention.

A probe is schematically shown in FIG. 1. A resonator sphere 11 is placed at a height or distance h from the surface 12 of the metal 13 to be tested. A coupling loop 14 provides high frequency field $h_{rf}$ to the resonator by means of rf current i flowing through the loop. A d.c. magnetic field $H_{DC}$ is provided orthogonal to the magnetic field $h_{rf}$. There is precession of the spins in the YIG material about the d.c. field, $H_{DC}$, because of the d.c. and rf magnetic fields. The precession is resonant about the d.c. bias field at a frequency which is determined by the magnitude of the d.c. field, $H_{DC}$, and the rf demagnetizing fields arising from the magnetic poles produced at the boundaries. The motion is excited by the rf currents producing the orthogonal field $h_{rf}$. The rf frequency can be swept through the resonant frequency. The resonant frequency can be observed when there is an absorption of energy from the rf field by the resonating atoms. Thus, by sweeping the frequency of the rf exciting current and detecting the amplitude, one can determine the frequency at which there is resonance.

It is known that if a metal is brought near the resonator eddy currents will be induced in the metal. These currents produce fields which are coupled to the resonator. These fields act as additional demagnetizing fields and cause an additional frequency shift in the resonator. Thus, if the resonator is maintained at a constant height h from the surface under test as the probe is moved over the surface, the so-called "wall effect" fields will remain uniform and the frequency will remain constant. However, if there is a flaw in the surface, the eddy currents will be interrupted and the reflected eddy current fields reduced. This will cause a shift in the resonant frequency which can be detected as a change in the frequency at which energy is absorbed by the resonator from the driving oscillator.

The relative frequency shift is $$\frac{\Delta f}{f} = \frac{-1}{2} \frac{\text{magnetic stored energy in the flaw}}{\text{magnetic stored energy in the resonator}}$$

The crack detection sensitivity is enhanced by reducing the volume of the resonator relative to the crack and by increasing its Q.

Figure 2:
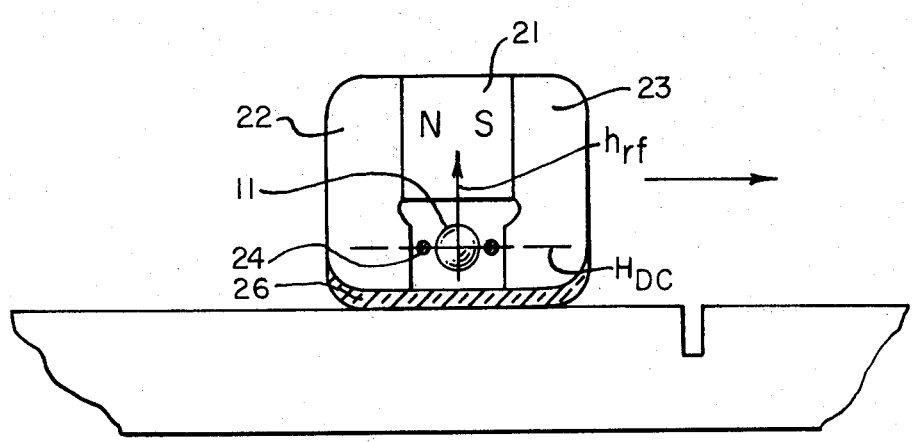
FIG. 2 schematically shows a probe in accordance with the present invention employing eddy current perturbation.

Referring to FIG. 2, there is schematically shown a probe in accordance with the invention. The probe includes a resonator 11. A magnet 21 provides d.c. magnetic field $H_{DC}$ through pole pieces 22 and 23. A coil 24 provides the orthogonal rf magnetic field $h_{rf}$. A thin plastic cover 26 provides a mechanical means for maintaining a uniform height h above the surface. Thus, in use, the probe can be brought into contact with the surface and moved therealong. As will be presently described, a change in height will provide an unwanted frequency shift.

Figure 3:
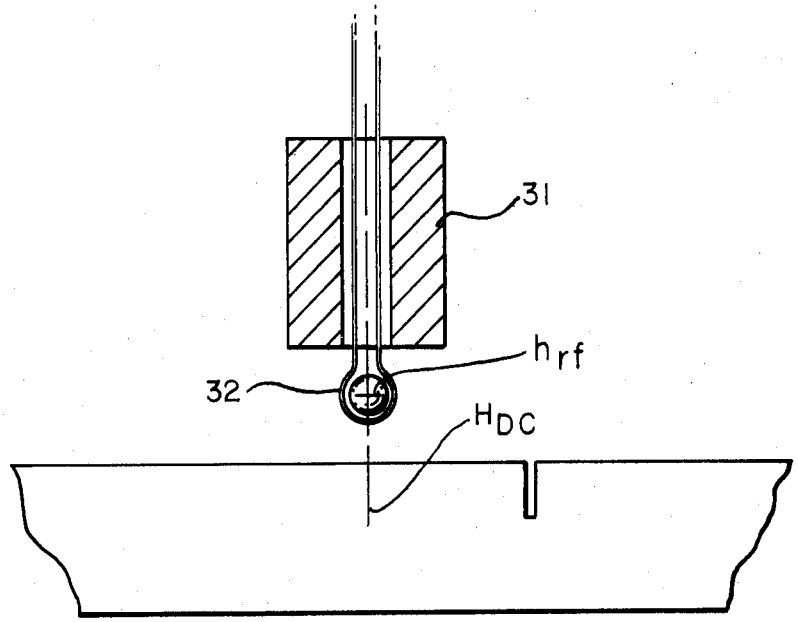
FIG. 3 schematically shows a probe in accordance with the present invention employing d.c. magnetic field and eddy current perturbations.

In FIG. 3 there is shown another embodiment of the present invention. This embodiment is suitable for detecting surface flaws in both magnetic and non-magnetic metals. A magnet 31 provides a d.c. magnetic field perpendicular to the surface to be tested. A coil 32 provides a magnetic field $h_{rf}$ substantially parallel to the surface and perpendicular to the d.c. magnetic field. A plastic cover (not shown) covers the resonator and determines the height during scanning of a metal.

As before, there is precession and resonance of the atoms under the influence of the d.c. and rf magnetic fields. However, rather than having the resonator fields perturbed only by the eddy current fields, they may also be perturbed by a change in the pattern of the d.c. field as the probe is scanned over the crack. It is seen that the field will be disturbed by the change in the configuration of the magnetic path adjacent the magnet 31 when the metal is magnetic. These changes will be reflected in the impedance of the resonator as reflected by absorption of energy from the coil.

The change in resonance of the resonator can also be detected by employing an additional coil about the resonator which is employed to sense the resonant frequency of the resonator by coupling to the resonator fields. The coil is located orthogonal to the excitation coil so that it is decoupled therefrom.

In use the probes are brought into contact with the metal surface to be tested, the frequency of the field $h_{rf}$ is varied over a predetermined range and the point of resonance is measured or detected. This is continuously done as the probe is scanned. When a defect or crack is encountered by the probe, a shift in resonant frequency is observed giving the desired indication.

One problem with each of the probes just described is that the induced magnetic fields or the disturbance of the magnetic fields is dependent upon the height h. Thus, in order to obtain meaningful data, it is necessary to maintain a substantially constant height h. This is done by providing the plastic shield which can engage the surface.

Figure 4:
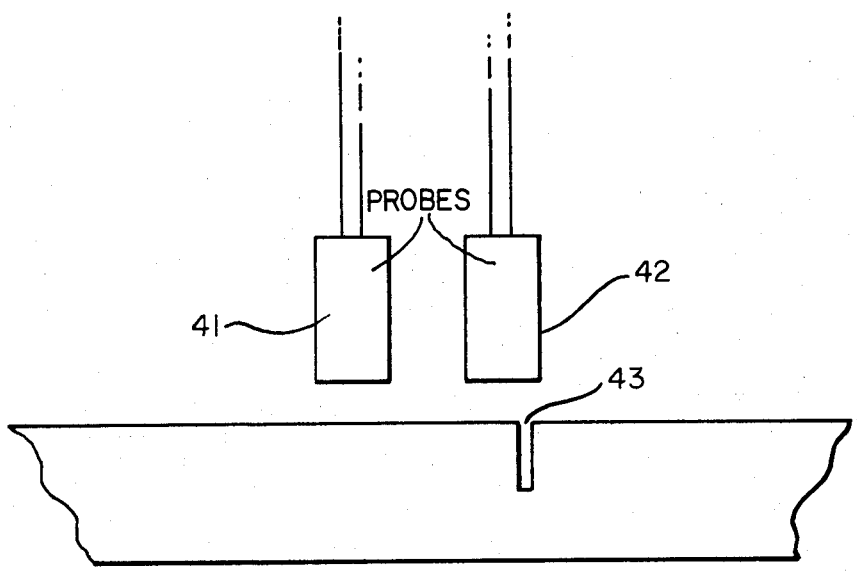
FIG. 4 schematically shows a probe assembly which is insensitive to variations in distance of the probe from the surface under test.

An alternative is to employ a pair of probes 41 and 42, FIG. 4, and to compare the frequencies at which resonance occurs. This frequency will be independent of the height h. However, if one probe is adjacent a flaw, its frequency or impedance will change with respect to the other and indicate the presence of the flaw, such as flaw 43.

It should be apparent to one skilled in the art that rather than sweeping the rf field to achieve resonance, the rf field may be maintained at a constant frequency and the strength of the d.c. magnetic field varied. This could be achieved by employing an electromagnet rather than a permanent magnet.

The resonator can be chosen to be relatively small whereby to provide good resolution. In addition, resonators of the type described are very sensitive to the demagnetization effect or changes in magnetic fields.

Thus, there has been provided a ferromagnetic resonance probe and method which has high resolution and sensitivity.

What is claimed is:

1. A probe for scanning a metal surface to test for flaws in the metal surface comprising a ferromagnetic resonator, means for applying a d.c. bias magnetic field, $H_{DC}$, to said resonator, means for applying an rf magnetic field $h_{rf}$ to said resonator orthogonally to said d.c. magnetic field, and means coupled to said resonator for detecting changes in the resonant frequency of said resonator responsive to flaws in the metal surface under test.

2. A probe as in claim 1 in which the d.c. field $H_{DC}$ is applied parallel to the surface under test.

3. A probe as in claim 1 in which the d.c. field $H_{DC}$ is applied perpendicular to the surface under test.

4. A probe as in claim 1 in which the means for detecting changes in the resonant frequency includes means for varying the frequency of the rf magnetic field and determining the frequency at which the resonator resonates.

5. A probe as in claim 1 in which means is provided for varying the strength of the d.c. magnetic field.

6. The method of detecting flaws in a metal surface which comprises the steps of disposing a ferromagnetic resonator adjacent the surface and scanning the surface, applying a d.c. magnetic field to said resonator, applying an rf magnetic field to said resonator, sweeping the frequency of the rf magnetic field so that it causes the resonator to resonate, determining the resonant frequency or impedance of said resonator when it is adjacent to the flawless surface and detecting changes in the resonant frequency or impedance as the resonator is disposed adjacent a flaw in the surface.

7. The method as in claim 6 wherein the d.c. magnetic field is applied with a component perpendicular to the surface.

8. The method as in claim 6 wherein the d.c. magnetic field is parallel to the surface.

9. The method of detecting flaws in a metal surface which comprises the steps of disposing a ferromagnetic resonator adjacent said metal surface, exciting said resonator so that it resonates at a frequency which is determined in part by the metal surface, and detecting changes in the resonant frequency induced by flaws in the metal surface.

* * * * *